United States Patent [19]
Sockell et al.

[11] Patent Number: 5,840,955
[45] Date of Patent: Nov. 24, 1998

[54] WASTE MINIMIZATION AND PRODUCT RECOVERY PROCESS

[76] Inventors: Edward J. Sockell, 806 Westwood, Port Lavaca, Tex. 77979; Joseph C. Sarna, 206 Waterford Dr., Victoria, Tex. 77901; Ali Kerr, 301 Brocton, Victoria, Tex. 77904; Sanjay P. Godbole, 7260 Winchester Dr., Solon, Ohio 44139

[21] Appl. No.: 977,762

[22] Filed: Nov. 25, 1997

[51] Int. Cl.⁶ .......................... C07C 253/00; C07C 255/00
[52] U.S. Cl. ............................................ 558/324; 558/435
[58] Field of Search ..................................... 558/324, 435

[56] References Cited

U.S. PATENT DOCUMENTS

| | | |
|---|---|---|
| Re. 32,484 | 8/1987 | Grasselli et al. . |
| 2,086,731 | 7/1937 | Millar et al. . |
| 2,634,825 | 4/1953 | Drake et al. . |
| 3,230,246 | 1/1966 | Callahan et al. . |
| 3,636,068 | 1/1972 | Lovett et al. . |
| 3,642,930 | 2/1972 | Grasselli et al. . |
| 3,885,928 | 5/1975 | Wu . |
| 3,895,050 | 7/1975 | Sheely . |
| 4,234,510 | 11/1980 | Wu . |
| 4,503,001 | 3/1985 | Grasselli et al. . |
| 4,767,878 | 8/1988 | Grasselli et al. . |
| 4,863,891 | 9/1989 | Grasselli et al. . |
| 5,093,299 | 3/1992 | Suresh et al. . |

*Primary Examiner*—Johann Richter
*Assistant Examiner*—Joseph Murray
*Attorney, Agent, or Firm*—David J. Untener; Brian L. Mehosky

[57] ABSTRACT

A process for the enhanced recovery of hydrogen cyanide (HCN) obtained from the reactor effluent of an ammoxidation reaction of propylene or isobutylene comprising passing the reactor effluent through a quench column, an absorber column, a first distillation column, a second distillation column, a cooler and a knock-out pot, wherein the improvement comprises contacting the vapor phase containing hydrogen cyanide with an aqueous stream.

9 Claims, No Drawings

WASTE MINIMIZATION AND PRODUCT RECOVERY PROCESS

FIELD OF THE INVENTION

The present invention is directed to an improved process for the manufacture of acrylonitrile or methacrylonitrile. In particular, the present invention is directed to the improvement in the recovery of hydrogen cyanide utilized during the manufacture of acrylonitrile or methacrylonitrile.

Recovery of acrylonitrile/methacrylonitrile produced by the ammoxidation of propylene or isobutylene on a commercial scale has been accomplished by quenching the reactor effluent with water followed by passing the gaseous stream containing acrylonitrile or methacrylonitrile resulting from the quench to an absorber where water and the gases are contacted in counter-current flow to remove substantially all the acrylonitrile or methacrylonitrile, the aqueous stream containing the acrylonitrile or methacrylonitrile and HCN is then passed through a series of distillation columns and associated decanters for separation and purification of product acrylonitrile or methacrylonitrile from a vapor stream containing substantially all the HCN.

Typical recovery and purification systems that are used during the manufacture of acrylonitrile or methacrylonitrile are disclosed in U.S. Pat. Nos. 4,234,510 and 3,885,928, assigned to the assignee of the present invention and herein incorporated by reference.

SUMMARY OF THE INVENTION

It is the primary object of the present invention to provide an improved process for the recovery of byproduct HCN in the manufacture of acrylonitrile or methacrylonitrile.

It is a further object of the present invention to provide an improved process for the manufacture of acrylonitrile or methacrylonitrile which reduces the amount of HCN directed to incineration or other recovery processes.

It is a further object of the present invention to provide an improved process for the manufacture of acrylonitrile or methacrylonitrile comprising transporting the reactor effluent obtained during the ammoxidation of propylene or isobutylene to a quench column wherein the hot effluent gases are cooled by contact with an aqueous spray, passing the cooled reactor effluent overhead to an absorber column wherein the crude acrylonitrile or methacrylonitrile is absorbed in water, passing the resulting vapor stream containing the HCN to a product cooler and then to a knockout pot, wherein the improvement comprises contacting the cooled HCN product with an aqueous stream.

It is a further object of the present invention to provide an improved process as described above wherein the aqueous stream is contacted with the cooled HCN product before the combined stream is introduced to the knock-out pot.

An additional object of the present invention to provide an improved process as described above wherein the aqueous stream is contacted with the cooled HCN product inside the knock-out pot.

It is a further object of the present invention to provide an improved process as described above wherein the aqueous stream is contacted with the cooled HCN product before the combined stream is introduced to the knock-out pot and inside the knock-out pot.

It is yet an additional object of the present invention to provide an improved process as described above wherein the reactor effluent is obtained from the ammoxidation of propylene, ammonia and oxygen to produce acrylonitrile.

Another object of the present invention to provide an improved process as described above wherein the reactor effluent is obtained by the reaction of propylene, ammonia and air in a fluid bed reactor while in contact with a fluid bed catalyst.

Additional objects, advantages and novel features of the invention will be set forth in part in the description which follows, and in part, will become apparent to those skilled in the art upon examination of the following or may be learned by the practice of the invention. The objects and advantages of the invention may be realized and obtained by means of the instrumentalities and combinations particularly pointed out in the appended claims. To achieve the foregoing and other objects and in accordance with the purpose of the present invention as embodied and broadly described herein, the process of the present invention comprises transporting the reactor effluent obtained during the ammoxidation of propylene or isobutylene to a quench column wherein the hot effluent gases are cooled by contact with an aqueous spray, passing the cooled reactor effluent overhead to an absorber column wherein the crude acrylonitrile or methacrylonitrile is absorbed in water, passing the aqueous solution containing the acrylonitrile or methacrylonitrile, plus HCN and other impurities to a first distillation column (recovery column), where a significant portion of the water and impurities are removed as a liquid bottoms product, while HCN, water, a minor portion of impurities and acrylonitrile or methacrylonitrile are removed as an overhead vapor stream. In past operations, this overhead vapor stream is further cooled using a heat exchanger, and directed to a knockout drum, to separate and condensed liquids which are returned to the recovery process, while the remaining vapor stream is directed to a flare, incinerator, or other disposal process.

The current invention improves the past operation by adding an aqueous stream to the cooled stream directed to the knock-out pot or, alternately, by adding an aqueous stream using spray nozzles inside the knock-out pot to contact the vapor stream. Optionally, aqueous streams may be added to the cooled stream as well as to the spray nozzles at the same time. The aqueous stream may be a portion of the aqueous stream used to cool the reactor effluent in the quench column, a portion of the aqueous stream used to absorb the acrylonitrile or methacrylonitrile in the absorber tower ("lean water"), or other aqueous process stream including fresh water or demineralized water. The liquid stream from the knock-out pot bottoms, including the recovered HCN, may be directed back to the quench tower by addition to the aqueous stream used to cool the reactor effluent in the quench column, or to the absorber tower by addition to the aqueous stream used to absorb the acrylonitrile or methacrylonitrile in the absorber tower, or elsewhere in the recovery process.

In a preferred embodiment of the present invention, the process is performed with the reactor effluent obtained from the ammoxidation of propylene, ammonia and oxygen to produce acrylonitrile.

In a still preferred embodiment of the present invention, the reactor effluent is obtained by the reaction of propylene, ammonia and air in a fluid bed reactor while in contact with a fluid bed catalyst. Conventional fluid bed ammoxidation catalyst may be utilized in the practice of the invention. For example, fluid bed catalyst as described in U.S. Pat. Nos. 3,642,930 and 5,093,299, herein incorporated by reference, may be utilized in the practice of the present invention.

The present invention allows for the more efficient operation during the recovery of HCN. The operation of the HCN product cooler and HCN knock-out pot within the temperature range set forth above results in increased recovery of HCN in the liquid product of the HCN knock-out pot, which can be recovered in the existing acrylonitrile or methacrylonitrile recovery and purification process. This improved recovery means that less HCN is directed to incineration, with the resulting decrease in emissions from waste gas combustion. Another advantage of the practice of the invention is that operation of the HCN product cooler and HCN knock-out pot in the temperature and pressure ranges set forth above leads to increased recovery of product HCN.

BRIEF DESCRIPTION OF THE DRAWING

FIG. 1 is a schematic representation of the process as it applies to the manufacture of acrylonitrile and improved recovery of HCN.

DETAILED DESCRIPTION OF THE INVENTION

The present invention will now be described in detail with reference to FIG. 1. The reactor effluent 11 obtained by the ammoxidation of propylene or isobutylene, ammonia and oxygen containing gas in a fluid bed reactor (not shown) while in contact with a fluid bed ammoxidation catalyst is transported to a quench column 10 via transfer line 11, wherein the hot effluent gases are cooled by contact with water spray, 14. The cooled effluent gas containing the desired product (acrylonitrile or methacrylonitrile, acetonitrile and HCN) is then passed into the bottom of an absorber column 20 via line 12 wherein the products are absorbed in water which enters absorber column 20 from the top via line 24. The non-absorbed gases pass from the absorber through pipe 22 located at the top of the absorber 20. The aqueous stream containing the desired product is then passed via line 23 from the bottom of absorber 20 to the upper portion of a first distillation column 30 (recovery column) for further product purification. The product is recovered from the top portion of recovery column 30 and sent to a second distillation column 40 (heads column) 40 via line 32, while water and other impurities are removed from the recovery column 30 via line 33. In the heads column 40, the HCN is taken overhead and removed from the column via line 42, cooled in overhead condenser 80, and the resulting material directed to reflux drum 50 via line 41. Liquid reflux from the reflux drum 50 is returned to the upper portion of the heads tower via line 53. Vapor phase material is removed from the reflux drum 50 via line 52 and cooled in HCN product condenser 90. The cooled and partially condensed effluent of the HCN product condenser 90 is directed to the HCN knock-out pot vial lines 93 and 61. Optionally, an aqueous stream may be added to the partially condensed effluent of the HCN product condenser via line 71, and the combined stream directed to the HCN knock-out pot via line 61. The HCN knock-out pot may, optionally, be fitted with one or more spray nozzles 73, to provide for the addition of an aqueous stream to the HCN knock-out pot via line 72. A significant portion of the HCN is condensed or absorbed by the added aqueous stream, and removed from the HCN knock-out pot via line 63 and returned to the recovery process. Optional locations where the condensed or absorbed HCN and added aqueous material, stream 63, may be returned to the recovery process include the quench tower 10 cooling water 14, absorber tower 20 absorber water 24, recovery column 30. Uncondensed HCN, along with other non-condensable material, is removed from the HCN knock-out pot vial line 62, and may be sent directly to an incinerator, or purified and recovered by conventional means known in the art. When the process is operated by adding an aqueous steam 72 to the knockout drum spray nozzles, the aqueous stream is contacted more efficiently in comparison with adding an aqueous stream 71 directly. Depending on the noncondensibles present in the vapor stream entering the knock-out pot, and the ratio of aqueous stream to the vapor stream, temperature of the stream exiting knock-out pot, it is possible to recover the hydrogen cyanide from the vapor stream over a wide range of recovery efficiencies.

During a flare analysis test it was observed that with the water addition system turned on in the knock-out pot, the amount of HCN going to flare decreased from 200 lb/hour to 100 lb/hr. The incoming vapor stream to the knock-out pot had 33.0 wt % HCN, 58.3 % Nitrogen, 4.12 % C02, 4.12 % CO and in this case had a mass flow of 600 lb / hour. A lean water flow of 3 gpm was used to the sprays.

The limit to the water addition simply is controlled by feasibility of the amount of solution to be removed from the knock-out pot as well as the constraint on additional waste water treatment.

The process simulations further show that tripling the water flow would increase the HCN recovery efficiency through the knock-out pot from 50 % to 84.5 %. If chilled water to a temperature of 55 F is used, the recovery efficiency could further be increased to 96%.

Preferably, the ammoxidation reaction is performed in a fluid bed reactor although other types of reactors such as transport line reactors are envisioned. Fluid bed reactors, for the manufacture of acrylonitrile are well known in the prior art. For example, the reactor design set forth in U.S. Pat. No. 3,230,246, herein incorporated by reference, is suitable.

Conditions for the ammoxidation reaction to occur are also well known in the prior art as evidenced by U.S. Pat. Nos. 5,093,299; 4,863,891; 4,767,878 and 4,503,001; herein incorporated by reference. Typically, the ammoxidation process is performed by contacting propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The typical molar ratio of the oxygen to olefin in the feed should range from 0.5:1 to 4:1, preferably from 1:1 to 3:1. The molar ratio of ammonia to olefin in the feed in the reaction may vary from between 0.5:1 to 5:1. There is really no upper limit for the ammonia-olefin ratio, but there is generally no reason to exceed a ratio of 5:1 for economic reasons.

The reaction is carried out at a temperature of between the ranges of about 260° to 600 ° C., but the preferred ranges being 310 ° to 500 ° C., especially preferred being 350 °to 480 ° C. The contact time, although not critical, is generally in the range of 0.1 to 50 seconds, with preference being to a contact time of 1 to 15 seconds.

In addition to the catalyst of U.S. Pat. No. 3,642,930, other catalysts suitable for the practice of the present invention are set forth in U.S. Pat. No. 5,093,299, herein incorporated by reference.

The conditions under which the absorber column, recovery column and heads column are maintained range between 1 to 7 psig (80°F. to 110° F.), 0.5 to 10 psig (155° F. to 170° F.), and −10 to 5 >psig (52° F. to 92° F.), respectively.

The present invention not only results in an unexpected improvement in the recovery rates of HCN but achieves this improvement without increasing the size of the columns utilized in the recovery and purification section. In addition, the attendant increase in production rates does not come with any observed deterioration in the product quality.

As will be evident to those skilled in the art, various modifications of this invention can be made or followed in light of the foregoing disclosure and discussion without departing from the spirit and scope of the disclosure or from the scope of the claims.

What is claimed is:

1. A process for the manufacture of acrylonitrile or methacrylonitrile comprising transporting the reactor effluent obtained during the ammoxidation of propylene or isobutylene to a quench column wherein the hot effluent gases are cooled by contact with an aqueous spray, passing the cooled reactor effluent overhead to an absorber column wherein the crude acrylonitrile or methacrylonitrile is absorbed in water, passing the resulting vapor stream containing the HCN to a product cooler and then to a knock-out pot, wherein the improvement comprises contacting the cooled HCN product with an aqueous stream.

2. The process of claim 1 wherein said aqueous stream is contacted with the cooled HCN product before the combined stream is introduced to the knock-out pot.

3. The process of claim 1 wherein said aqueous stream is contacted with the cooled HCN product inside the knock-out pot.

4. The process of claim 1 wherein said aqueous stream is contacted with the cooled HCN product before the combined stream is introduced to the knock-out pot and inside the knock-out pot.

5. The process of claim 1 wherein said aqueous stream is lean water.

6. The process of claim 1 wherein said aqueous stream is fresh water.

7. The process of claim 1 wherein said aqueous stream is demineralized water.

8. The process of claim 1 wherein the reactor effluent is obtained from the ammoxidation of propylene, ammonia and oxygen to produce acrylonitrile.

9. The process of claim 1 wherein the reactor effluent is obtained by the reaction of propylene, ammonia and air in a fluid bed reactor while in contact with a fluid bed catalyst.

* * * * *